United States Patent [19]

Zimmerman et al.

[11] Patent Number: 5,496,538

[45] Date of Patent: Mar. 5, 1996

[54] SELF-FOAMING CLEANSER

[75] Inventors: Amy C. Zimmerman, Ansonia, Conn.; David A. Rosser, Heswall, United Kingdom

[73] Assignee: Chesebrough-Pond's USA Co., Division of Conopco, Inc., Greenwich, Conn.

[21] Appl. No.: 304,717

[22] Filed: Sep. 12, 1994

Related U.S. Application Data

[62] Division of Ser. No. 110,275, Aug. 23, 1993, Pat. No. 5,443,817.

[51] Int. Cl.$^6$ .............................. A61K 7/00; A61K 9/12
[52] U.S. Cl. .................... 424/45; 424/47; 424/73; 424/401; 424/70.9; 514/945; 514/937; 514/972
[58] Field of Search .......................... 424/45, 47, 73, 424/401, 70.9; 514/945, 937, 972

[56] References Cited

U.S. PATENT DOCUMENTS

| | | | |
|---|---|---|---|
| 2,610,940 | 9/1952 | Endicott | 424/45 |
| 2,728,495 | 12/1955 | Eaton | 424/47 |
| 2,742,321 | 4/1956 | Mina et al. | 424/47 |
| 3,719,752 | 3/1973 | Taylor | 424/47 |
| 3,840,465 | 10/1974 | Knowles et al. | 424/47 |
| 3,943,234 | 3/1976 | Roggenkamp | 252/142 |
| 3,970,584 | 7/1976 | Hart et al. | 424/45 |
| 4,595,522 | 6/1986 | Bartlett et al. | |
| 4,708,813 | 11/1987 | Snyder | 252/90 |
| 4,806,262 | 2/1989 | Snyder | 252/90 |
| 5,002,680 | 3/1991 | Schmidt et al. | 252/90 |
| 5,137,715 | 8/1992 | Hoshowski et al. | 424/70.1 |
| 5,160,739 | 11/1992 | Kanga | 424/401 |
| 5,169,622 | 12/1992 | Kopolow et al. | 424/47 |

*Primary Examiner*—Thurman K. Page
*Assistant Examiner*—Raj Bawa
*Attorney, Agent, or Firm*—Milton L. Honig

[57] ABSTRACT

A sprayable cosmetic product is provided that includes a clear bottle capable of withstanding at least 10 psig fitted with a spray nozzle, and a clear, single-phase cosmetic composition. The cosmetic composition will contain a hydrocarbon propellant and a concentrate which may contain α-olefin sulphonate salts, alkyl polyglucosides and betaines as well as mixtures thereof. Upon activation of the spray nozzle, a thick, creamy mousse is expressed. The cosmetic compositions preferably will have a pH ranging from about 3.0 to 6.5. Best aesthetic appeal is achieved with a red dye which has been stabilized with a UV absorbing agent.

4 Claims, No Drawings

SELF-FOAMING CLEANSER

This is a divisional application of Ser. No. 08/110,275 filed Aug. 23, 1993, now U.S. Pat. No. 5,443,817 issued on Aug. 22, 1995.

BACKGROUND OF THE INVENTION

1. Field of the Invention

The invention concerns a cosmetic cleanser, especially for application to the face.

2. The Related Art

Properly formulated cleansers will effectively and efficiently remove previously applied face powder, rouge, foundation bases, eyeshadow and lipstick. Commercial facial cleansers depend on surfactant ingredients. These surfactants, when contacted with water, sometimes generate a bubbly foam. The cleansers of commerce are usually found in either a gel, lotion or cream form. There is, however, a continual search for less traditional forms that would provide an aesthetically pleasing presentation.

There was recently disclosed in U.S. Pat. No. 5,002,680 (Schmidt et al) a skin-cleansing mousse comprising an aerosol dispenser containing an emulsion formed from a concentrate and 3 to 12% by weight of a propellant. The concentrate requires an anionic or amphoteric surfactant, e.g. lauramido/myristamidopropyl betaine or a lauryl sarcosinate, a cationic polymer and an occlusive or nonocclusive moisturizer. These formulas are not believed to be single phase. Invariably, the concentrate-propellant compositions leading to mousses are packaged in opaque, pressure-resistant, metal cans. Aesthetic visual focus of mousse products is generally on the resulting creamy foam rather than the delivery system or concentrate upon which they depend.

Accordingly, it is an object of the present invention to provide a new format for delivery of a skin cleanser.

It is another object of the present invention to maintain an alcohol-free, single-phase liquid concentrate for a mousse format.

It is still another object of the present invention to provide a mousse product derived from a concentrate whose color is stabilized against degradation by light.

These and other objects of the present invention will more readily become apparent from the description and examples which follow.

SUMMARY OF THE INVENTION

A sprayable cosmetic product is provided including:
(i) a clear bottle capable of withstanding at least 10 psig, the bottle including at an open mouth thereof a spray nozzle; and
(ii) a clear, single-phase cosmetic composition including:
  (a) from about 0.5 to about 10% of a hydrocarbon propellant; and
  (b) from about 0.5 to about 40% of at least one surfactant in an aqueous medium; and
wherein upon actuation of the spray nozzle, a creamy foam mousse is expressed from the bottle.

In another aspect of the present invention there is provided a sprayable cosmetic product including:
(i) a clear bottle capable of withstanding at least 10 psig, the bottle including at an open mouth thereof a spray nozzle; and
(ii) a clear, single-phase cosmetic composition including:
  (a) from about 0.5 to about 10% of a hydrocarbon
  (b) from about 0.5 to about 40% of a $C_8$–$C_{30}$ α-olefin sulphonate salt in an aqueous medium sufficiently acidic that the composition has a pH between 3.0 and 6.5; and
wherein upon actuation of the spray nozzle, a creamy foam mousse is expressed from the bottle.

In a still further aspect of the present invention there is provided a sprayable cosmetic product including:
(i) a clear bottle capable of withstanding at least 10 psig, the bottle including at an open mouth thereof a spray nozzle;
(ii) a clear, single-phase cosmetic composition including:
  (a) from about 0.5 to about 10% of a hydrocarbon propellant;
  (b) a water-soluble organic aye present in an amount sufficient to impart a visible color to the composition; and
  (c) a UV absorber in the 300 to 400 nm range present in a sufficient amount to prevent fading of the dye upon storage; and
wherein upon actuation of the spray nozzle, a creamy foam mousse is expressed from the bottle.

DETAILED DESCRIPTION OF THE INVENTION

Now there has been developed a self-foaming cleanser based on a cosmetic composition that aesthetically interacts with a dispensing package. More specifically, there is provided a clear, single phase liquid cosmetic composition containing propellant gases held within a clear, pressurizable bottle fitted with a spray nozzle. Upon observing the clear liquid through the trans-parent bottle, a consumer anticipates a mist-like spray aerosol to be generated upon compression of the spray nozzle. Much to the user's astonishment, a creamy foam mousse, resembling shaving cream in consistency, is expressed through the nozzle upon actuation thereof.

According to the invention, a first essential component is that of a clear bottle pressurizable to the extent that the bottle can withstand at least 10 psig, preferably at least from 25 to 50 psig pressure. Suitable for this purpose is a glass bottle sold by the Wheaton Glass Company, Model M937F. The preferred embodiment will include a clear, plastic coating (0.01 to 0.1 inches thick), such as polyvinyl chloride (preferred mode), polyolefin, polyacrylate or polyurethane, fully surrounding an exterior surface of the glass bottle. A standard aerosol spray nozzle will be fitted within a mouth of the bottle, normally crimped therewithin to establish a pressure resistant seal.

A second essential element of the product according to the present invention is that of a clear, single-phase cosmetic composition. The cosmetic composition will normally fill anywhere from 30 to 99% of the bottle capacity. This composition will include a concentrate in an amount from about 80 to about 99.5%, preferably from about 87 to about 97% by weight, and a hydrocarbon propellant in an amount from about 0.5 to 10%, preferably from about 1 to less than 3%, optimally about 1.5 to 2.8% by weight.

The term "clear" is intended to be synonymous with transparent. More technically this is defined as a material having a maximum transmittance of light of at least 4% of any wavelength in the range of 200 to 800 nm through a sample 10 cm thick. A clear or transparent composition or glass is one which also permits sufficient light transmittance to enable reading of newspaper print through a thickness commensurate with the diameter of a bottle pursuant to the claimed invention.

Propellant for use with the cosmetic compositions of the present invention advantageously are low boiling point (less than 50° C.) hydrocarbons. Most preferred is a purely isobutane propellant such as A31. Less preferred is an isobutane/isopropane mixture such as propellant A45.

An essential element in achieving a single phase cosmetic composition is that the propellant be agitated with the concentrate either mechanically or through a technique such as ultrasound. Addition of hot, i.e. at least 35° C., concentrate into the propellant or vice versa may also accomplish dispersion into a single, clear phase.

Concentrates of the present invention will include water as the major component. Water will range in an amount from about 30 to about 98%, preferably from about 50 to about 95%, optimally from about 80 to 85% by weight of the total cosmetic composition.

Cosmetic compositions of the present invention will preferably exhibit a pH from about 3.9 to about 6.5, more preferably from about 3.5 to about 5.0, optimally from about 4.5 to 5.0.

Surfactants will also be present in the cosmetic compositions of the present invention. Total concentration of the surfactant will range from about 0.5 to about 40%, preferably from about 7 to about 20%, optimally from about 5 to no higher than 10% by weight of the total cosmetic composition. Each individual surfactant may be present in an amount from about 0.5 to about 20%, preferably no higher than about 10% by weight. The surfactant may be selected from the group consisting of anionic, cationic, nonionic and amphoteric actives. Especially useful is a combination of an anionic and an amphoteric surfactant in a relative weight ratio from about 5:1 to 1:5, preferably from about 3:1 to 1:3, optimally from about 2:1 to 1:1. Even more preferred is the further addition of a nonionic surfactant such that the ratio of total anionic and amphoteric to nonionic surfactant ranges from about 10:1 to 1:10, preferably from about 5:1 to 1:1, optimally from about 4:1 to 2:1 by weight.

When the concentrate is held at a pH of no higher than 5.0, it is advantageous to employ a $C_8$–$C_{30}$ α-olefin sulphonate salt as the anionic surfactant. Salt cations to be used with the sulphonate may be selected from alkali metals, ammonium and $C_1$–$C_{20}$ alkanolammonium ions. In general, it is advantageous that the anionic surfactants of the present invention all exhibit an HLB of at least 15.

Representative of the amphoteric surfactant category are the $C_8$–$C_{30}$ amine oxides and betaines. Illustrative of the latter type are the $C_8$–$C_{30}$ fatty alkyl amido betaines, sulphobetaines and mixtures thereof. Most preferred is cocoamidopropyl betaine.

Advantageously, the concentrate will also contain a nonionic surfactant, especially a $C_6$–$C_{20}$ alkyl polyglucoside, an example of which is Plantareen 2000® available from the Henkel Corporation of Ambler, Pa. Polyglucosides assist the anionic surfactant to solubilize the propellant and significantly improve mildness of the cosmetic composition.

Coupling agents may also be included within the compositions of the present invention. These agents will normally be polypropoxylated $C_8$–$C_{20}$ fatty alcohols or fatty acids. Suitable for purposes of this invention are PPG-Steareth-15 and PPG-2Isoceteath-20 Acetate. The coupling agent may be present in amounts ranging from about 0.1 to about 5%, preferably between about 0.5 and 2%, optimally between 0.8 and 1.2% by weight of the composition.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by weight Of the composition.

With certain combinations of component materials, the cosmetic compositions of the present invention may also include a $C_1$–$C_4$ monohydric alcohol. Levels of the monohydric alcohol may range from about 1 to about 40% by weight of the composition. Preferably, however, the compositions should be essentially free of monohydric alcohols such as ethanol. In tests evaluating certain of the cosmetic compositions, the presence of ethanol suppressed the fragrance emitted upon formation of mousse as this was being generated from the spray nozzle.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.1 to about 8%, optimally between about 0.1 and 1% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives are and routinely choose them to satisfy the preservative challenge test and to provide product stability. Particularly preferred preservatives are methyl paraben, imidazolidinyl urea, sodium dehydroxyacetate, propyl paraben and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Compounds that can provide α-hydroxyacids upon hydrolysis may also be useful as components of the cosmetic composition. In particular, $C_8$–$C_{30}$ acyl lactylate and salts thereof may be employed. The alkalimetal, ammonium and $C_1$–$C_{12}$ alkanolammonium salts are most effective. Amount of the lactylate may range from about 0.1 to about 10%, preferably from about 0.2 to about 3%, optimally between about 0.5 and 1.5% by weight of the cosmetic composition.

When compositions of the present invention include as surfactant a mixture of α-olefin sulphonate salt and alkyl polyglucoside, the ratio will be about 10:1 to 1:10, preferably 3:1 to 1:3, optimally between about 1:2 and 1:1 by weight.

Minor adjunct ingredients may also be present in the cosmetic compositions. These ingredients include vitamins (such as vitamin E acetate, vitamin A palmitate and DL-panthenol), fragrances and thickeners. Levels of fragrance may range from about 0.05 to about 5%, preferably 0.1 and 1% by weight.

In another aspect of the present invention, there has been discovered a problem with stability of colorants incorporated as minor ingredients in the cosmetic composition. By the term colorants is meant any water-soluble dye which imparts a color in the visible range to that of the composition. Colors may include red, yellow, blue and green as well as shades therebetween. Most preferred, however, are the red or pink dyes. Illustrative of this category are FD&C Red NO. 3, Red NO. 4, Red NO. 40 and the D&C colorants Red No. 6, Red No. 28 and Red NO. 33. Most preferred is Red No. 33. Active levels of this material may range from about 0.001 to about 1%, preferably between about 0.01 and about 0.1% by weight.

Colored compositions of the present invention may fade over time when exposed to sunlight penetrating the clear bottles. This problem has been solved by incorporation of a stabilizing agent capable of absorbing ultraviolet radiation in the 300 to 400 nm range. Stabilizers may be selected from the para-amino benzoates, salicylates, cinnamates, benzophenones, anthralinates, azoles and digalloyl functional groups. Levels of the color stabilizing agents may range from about 0.001 to about 5%, preferably from about 0.001 to about 0.5%, optimally between about 0.02 and 0.1% by weight. The colorant and the color stabilizing agent are preferably water-soluble materials. Especially useful as the color stabilizing agent is butyl methoxydibenzoylmethane (CTFA nomenclature) available from the Givaudan-Roure Corporation under the trademark Stabilizer 89®.

The following Examples will more fully illustrate the embodiments of this invention. All parts, percentages and proportions referred to herein and in the appended claims are by weight unless otherwise indicated.

EXAMPLES 1

A series of concentrates are listed in Table I which illustrate typical formulations of the present invention. These concentrates were then combined with A31 propellant in a weight amount of 97:3, respectively. Propellant and concentrate were then vigorously shaken to form a single phase transparent liquid. The resulting cosmetic compositions were then packaged into a Wheaton Model 937F pressure-resistant glass bottle. A spray nozzle head was then inserted into the mouth of the bottle and crimped around the mouth to achieve a pressure seal.

TABLE I

| TRADEMARK | CTFA Nomenclature | WEIGHT %* | | | | | |
|---|---|---|---|---|---|---|---|
| | | 1 | 2 | 3 | 4 | 5 | 6 |
| Glycerin | Glycerin | 6.00 | 6.00 | 6.00 | 6.00 | 6.00 | 6.00 |
| Bioterge AS-40 | SODIUM α-Olefin Sulfonate | 6.80 | 4.00 | 2.80 | 5.16 | 4.76 | 5.16 |
| Plantareen 2000 | $C_6$—$C_{12}$/$C_{10}$—$C_{16}$ Alkyl Polyglucoside | — | 2.80 | 1.98 | 1.70 | 3.30 | 1.70 |
| Tegobetaine C | Cocoamidopropyl Betaine | 3.30 | 3.30 | 3.30 | 3.30 | 3.30 | 3.30 |
| — | PPG-2 Isocetheth-20 Acetate | 1.00 | 1.00 | 1.00 | 1.00 | 1.00 | 1.00 |
| Pationic 138C | Sodium Lauroyl Lactylate | 0.50 | 0.50 | 0.50 | 0.50 | 0.50 | 0.50 |
| Glypure | Glycolic Acid | 0.36 | 0.36 | 0.36 | 0.36 | 0.36 | 0.36 |
| — | Ammonium Hydroxide | 0.13 | 0.13 | 0.13 | 0.13 | 0.13 | 0.13 |
| — | Fragrance | 0.16 | 0.16 | 0.16 | 0.16 | 0.16 | 0.16 |
| — | α-Hydroxycaprylic Acid | 0.05 | 0.05 | 0.05 | 0.05 | 0.05 | 0.05 |
| — | FD & C Red No. 33 | 0.03 | 0.03 | 0.03 | 0.03 | 0.03 | 0.03 |
| Glydant Plus | DMDM Hydantoin | 0.10 | 0.10 | 0.10 | 0.10 | 0.10 | 0.10 |
| Stabilizer 89 | Butyl Methoxydibenzoylmethane | 0.05 | 0.05 | 0.05 | — | 0.05 | 0.05 |
| — | Vitamin E Acetate | 0.05 | 0.05 | 0.05 | 0.05 | 0.05 | 0.05 |
| — | DL-Panthenol | 0.05 | 0.0.5 | 0.05 | 0.05 | 0.05 | 0.05 |
| — | Benzophenone-4 | — | — | — | 0.05 | — | — |
| — | SD40 Alcohol | — | — | — | — | — | 5.00 |
| — | Water | BALANCE | | | | | |

*Listed as % active

All the foregoing Examples formed clear fluid compositions and exhibited a pH between 4.7 and 4.9.

Although this invention has been described with reference to specific Examples, it will be apparent to one Skilled in the art that various modifications will be suggested, all of which are within the spirit and purview of this invention.

What is claimed is:

1. A sprayable cosmetic product comprising:
   (i) a clear bottle capable of withstanding at least 10 psig, the bottle including at an open mouth thereof a spray nozzle;
   (ii) a clear, single-phase cosmetic composition filling anywhere from 30 to 99% of the bottle, comprising:
      (a) from about 0.5 to about 10% by weight of a hydrocarbon propellant having a boiling point less than 50° C.;
      (b) from about 0.001 to about 1% by weight of a water-soluble organic dye;
      (c) from about 0.5 to about 40% by weight of a surfactant;
      (d) from about 0.001 to about 5% by weight of a UV absorber in the 300 to 400 nm range ; and
      (e) from about 30 to about 98% by weight of water;
   wherein upon actuation of the spray nozzle, a creamy foam mousse is expressed from the bottle.

2. A cosmetic product according to claim 1 wherein the dye is selected from the group consisting of FD&C Red No. 3, Red No. 4 and Red No. 33.

3. A cosmetic product according to claim 1 wherein the UV absorber is present in an amount from about 0.02 to about 0.1% by weight.

4. A cosmetic product according to claim 1 wherein the UV absorber is selected from the group consisting of para-amino benzoates, salicylates, cinnamates, benzophenones, anthralinates, azoles, digalloyl and mixtures thereof.

* * * * *